(12) United States Patent
Wu et al.

(10) Patent No.: US 9,310,316 B2
(45) Date of Patent: Apr. 12, 2016

(54) SELECTING PARAMETERS FOR DEFECT DETECTION METHODS

(75) Inventors: Kenong Wu, Davis, CA (US); Chris W. Lee, Fremont, CA (US); Michael J. Van Riet, Sunnyvale, CA (US); Yi Liu, Milpitas, CA (US)

(73) Assignee: KLA-Tencor Corp., Milpitas, CA (US)

( * ) Notice: Subject to any disclaimer, the term of this patent is extended or adjusted under 35 U.S.C. 154(b) by 457 days.

(21) Appl. No.: 13/610,658

(22) Filed: Sep. 11, 2012

(65) Prior Publication Data

US 2014/0072203 A1    Mar. 13, 2014

(51) Int. Cl.
G06K 9/00 (2006.01)
G01N 21/95 (2006.01)

(52) U.S. Cl.
CPC .................................. *G01N 21/9501* (2013.01)

(58) Field of Classification Search
CPC ................................................. G01N 21/9501
See application file for complete search history.

(56) References Cited

U.S. PATENT DOCUMENTS

| | | | |
|---|---|---|---|
| 5,900,633 A * | 5/1999 | Solomon et al. | 250/339.08 |
| 6,382,789 B1 | 5/2002 | Baudart et al. | |
| 6,674,888 B1 * | 1/2004 | Duzy | 382/148 |
| 6,687,527 B1 | 2/2004 | Wu et al. | |
| 7,570,797 B1 * | 8/2009 | Wang et al. | 382/145 |
| 8,000,922 B2 | 8/2011 | Chen et al. | |
| 8,135,204 B1 * | 3/2012 | Chen et al. | 382/141 |
| 2005/0033528 A1 * | 2/2005 | Toth et al. | 702/35 |
| 2006/0287751 A1 | 12/2006 | Dishner et al. | |
| 2008/0094639 A1 * | 4/2008 | Widmann et al. | 356/601 |
| 2008/0281548 A1 * | 11/2008 | Algranati et al. | 702/123 |
| 2009/0222753 A1 * | 9/2009 | Yamaguchi et al. | 715/771 |
| 2009/0281753 A1 * | 11/2009 | Noy | 702/81 |
| 2009/0299681 A1 * | 12/2009 | Chen et al. | 702/123 |
| 2010/0226561 A1 * | 9/2010 | Fujikawa et al. | 382/141 |
| 2011/0320149 A1 | 12/2011 | Lee et al. | |

FOREIGN PATENT DOCUMENTS

| | | |
|---|---|---|
| JP | 2005-501624 | 1/2005 |
| WO | 2007/023502 | 3/2007 |

OTHER PUBLICATIONS

International Search Report and Written Opinion for PCT/US2013/058790 mailed Dec. 27, 2013.

* cited by examiner

*Primary Examiner* — Stephen R Koziol
*Assistant Examiner* — Sean Conner
(74) *Attorney, Agent, or Firm* — Ann Marie Mewherter (57) ABSTRACT

Computer-implemented methods, computer-readable media, and systems for selecting one or more parameters for a defect detection method are provided. One method includes selecting one or more parameters of a defect detection method using an optimization function and information for a set of classified defects, which includes defects of interest and nuisance defects, such that the one or more parameters satisfy an objective for the defect detection method.

35 Claims, 3 Drawing Sheets

SELECTING PARAMETERS FOR DEFECT DETECTION METHODS

BACKGROUND OF THE INVENTION

1. Field of the Invention

This invention generally relates to selecting one or more parameters for a defect detection method applied to semiconductor wafer inspection.

2. Description of the Related Art

The following description and examples are not admitted to be prior art by virtue of their inclusion in this section.

Inspection processes are used at various steps during a semiconductor manufacturing process to detect defects on wafers. Semiconductor foundries manufacture various integrated circuit (IC) products for numerous fabless semiconductor companies. Defect types are different on different devices and layers. Inspection for many different types of defects has become more important recently. In some instances, a system that is configured to detect different types of defects may have adjustable sensitivity (or defect detection) parameters such that different parameters can be used to detect different defects or avoid sources of unwanted (nuisance) events. The efficiency in finding the right set of sensitivity parameters for a specific inspection objective is critical to inspection recipe setup.

Although an inspection system that has adjustable sensitivity parameters presents significant advantages to a semiconductor device manufacturer, these inspection systems are essentially useless if incorrect sensitivity parameters are used for an inspection process. Inspection sensitivity optimization is performed manually today. The user classifies defects, which serve as the "ground truth," specifies sensitivity parameters based on classified defects, runs inspection or inspection simulation such as Visual Optimizer (VO), which is commercially available from KLA-Tencor, Milpitas, Calif., and then looks at the inspection result. If the result is not satisfied, another round of parameter tuning is performed. VO provides visual feedback of the defect count or density distribution as well as the inspection simulation results. This parameter tuning process is performed iteratively until the result satisfies the user's objective, which is usually measured by defect of interest (DOI) capture and nuisance suppression. If the result cannot satisfy the detection objective, the user may change inspection imaging mode, such as spectrum, aperture, pixel size, focus, scan speed, etc. Another round of sensitivity tuning will be performed. This larger loop is also an iterative process. The number of iterations in the parameter tuning loop (inner loop) is orders of magnitude larger than combinations of the two outer loops. Automatic segmented auto thresholding (AutoSAT), which is commercially available from KLA-Tencor, can optimize SAT inspection recipes automatically.

As the semiconductor design rule is shrinking, DOI become smaller and smaller. To find such defects, more sophisticated defect inspection algorithms and more specialized optical modes are required. It is more and more difficult for general inspection tool users to fully comprehend and effectively tune the algorithms, especially in cases where a single optical mode does not adequately detect the DOI. Because of this complexity, the recipe set up time is getting longer and quality is much more subject to human-related factors, such as knowledge, experience, and skills. Inexperienced users may easily produce inconsistent or low quality recipes.

Multi-channel and multi-pass inspections challenge even experienced users. For example, there are three detection channels in Puma, a dark field inspection tool, commercially available from KLA-Tencor. The user currently sets up the recipe parameters channel by channel. If a defect is detected in one channel, the defect is detected by the inspection. It is not necessary to detect the same defect in another channel. It is almost impossible for a human user, taking the channel-by-channel approach, to fully leverage the parameter value in two other channels when tuning a parameter in the current channel. This approach limits the user's ability to take advantage of multi-channel inspection. Each iteration of manual tuning of a sensitivity recipe usually takes from many minutes to hours. To set up a production recipe, the user may go through many iterations, which may take days to complete.

AutoSAT is the first attempt to address the issue of automatic tuning sensitivity recipes. It optimizes the threshold parameters on a segment-by-segment basis. Here, a "segment" refers to a group of pixels within an image gray level range. The segment parameters are determined manually before AutoSAT is run. Its optimization engine cannot optimize segments and thresholds simultaneously. Since it does exhaustive searching in many sub-spaces of the full parameter set, it does not address the issue of recipe stability. AutoSAT is currently limited to the SAT algorithm. It cannot be applied to other algorithms.

Accordingly, it would be advantageous to develop methods and/or systems for selecting one or more parameters for one or more defect detection methods or algorithms that do not have one or more of the disadvantages described above.

SUMMARY OF THE INVENTION

The following description of various embodiments is not to be construed in any way as limiting the subject matter of the appended claims.

One embodiment relates to a computer-implemented method for selecting one or more parameters for a defect detection method. The method includes acquiring information for a set of classified defects. The classified defects were detected on a wafer using an inspection system. The classified defects include defects of interest (DOI) and nuisance defects. The method also includes acquiring an objective for a defect detection method. The defect detection method is to be applied to output generated for wafers by one or more detectors of an inspection system to thereby detect defects on the wafers. The objective is specified by a user. In addition, the method includes selecting one or more parameters of the defect detection method using an optimization function and the information for the set of classified defects such that the one or more parameters satisfy the objective. Acquiring the information, acquiring the objective, and selecting the one or more parameters are performed using a computer system.

The method described above may be performed as described further herein. In addition, the method described above may include any other step(s) of any other method(s) described herein. Furthermore, the method described above may be performed by any of the systems described herein.

Another embodiment relates to a computer-readable medium storing program instructions executable on a computer system for performing a computer-implemented method for selecting one or more parameters for a defect detection method. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to select one or more parameters for a defect detection method. The system includes an inspection system configured to detect defects on a wafer. The system also includes a computer system configured to perform the steps of the method described above. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a computer-implemented method for selecting one or more parameters for a defect detection method. The defect detection method may be performed by a defect detection algorithm. Therefore, the one or more parameters that are selected by the embodiments described herein may be one or more parameters of a defect detection algorithm. Although some embodiments or examples are described herein with respect to an algorithm, it is to be understood that the embodiments may be used to select one or more parameters for any defect detection method performed using an algorithm or some other function(s). In addition, the defect detection method may be performed by one or more defect detection algorithms. Therefore, the one or more parameters that are selected by the embodiments described herein may be one or more parameters of the one or more defect detection algorithms. Unless otherwise noted, all of the defect detection algorithms described herein are available on and/or used by wafer inspection tools commercially available from KLA-Tencor, Milpitas, Calif. For example, MDAT stands for Multi-Die Automatic Thresholding. HLAT stands for Hierarchical and Local Automatic Thresholding. FAST stands for Fast Adaptable Single Threshold. They are defect detection algorithms available on and/or used by wafer inspection tools commercially available from KLA-Tencor, Milpitas, Calif.

The method includes acquiring information for a set of classified defects. The classified defects were detected on a wafer using an inspection system. The classified defects include defects of interest (DOI) and nuisance defects. The set of classified defects preferably includes both DOI and nuisance defects (possibly in combination with other defect types) such that all types of defects are considered in the parameter selection described further herein. The DOI may include all defect types of interest. In addition, the set of classified defects may include defect types that the user wants to suppress (e.g., real defects that the user does not care about) and defects having unknown defect types. The defects may be classified into DOIs, real defects, and nuisance defects by a user. The defects may be detected on the wafer as described further herein, and the inspection system may be configured as described further herein.

The information for the set of classified defects may be acquired based on input from a user. For example, a user may click a browse button in a graphical user interface (GUI) used to perform the embodiments described herein to load a classified lot result. The classified lot result may be in a variety of different file formats such as defects.bin and SATfeatures.bin for the MDAT algorithm. The user may also provide a number of other input using the GUI such as specifying superclass codes and weights for each manual class of defects, a region ID, and a number of segments (for MDAT only).

In one embodiment, acquiring the information includes selecting one or more optics modes for the inspection system to be used for the wafer, detecting defects on the wafer using the one or more optics modes, and classifying the detected defects to thereby create the set of classified defects. As used herein, a "mode" or an "optics mode" generally refers to a single optical combination that includes a number of optical components including, but not limited to, a wavelength filter, one or more polarization filters, an aperture, and an objective set. In this manner, an optics mode may be defined by the parameters of various optical components of the inspection system that are or can be used in combination to scan a wafer thereby acquiring output for the wafer. Therefore, an optics mode as described herein effectively includes one or more (optical) parameters for inspection of a wafer.

Selecting the one or more optics modes in this embodiment may be performed using one step threshold setup (OSTS), which may be performed as described in U.S. Pat. No. 8,000, 922 to Chen et al., and which provides a user friendly method of quickly collecting data required to perform offline tuning of sensitivity parameters. It does this by collecting defect event candidates across the range of detection space so that they can be analyzed collectively instead of one at a time. It also helps remove much of the guess work required in setting a hot scan threshold producing more consistent, complete results. Auto-OSTS automates this method so that a user need not be present on the tool to perform the scan. The embodiments described herein may include any other step(s) of any other method(s) described in the above-referenced patent, which is incorporated by reference as if fully set forth herein. In addition, the embodiments described herein extend the original scope of Auto-OSTS by using the OSTS scan results to drive both sensitivity parameter optimization (via simultaneous sensitivity tuning (SST)) and optics selection (via optical selection (OS) with overall scoring), both of which may be performed as described further herein.

Detecting the defects on the wafer and classifying the detected defects in this embodiment may be performed as described further herein.

In one such embodiment, detecting the defects on the wafer using the one or more optics modes includes performing a hot scan on the wafer using the one or more optics modes and one or more defect detection algorithms. A "hot scan" generally refers to a scan/inspection of a wafer performed to detect defects on the wafer by applying relatively aggressive detection settings (e.g., thresholds substantially close to the noise floor). In this manner, the hot scan may be performed to collect inspection data about the wafer that will be used for the tuning process (optics selection and algorithm tuning). The goal of the hot scan is to detect a representative sample of all defect and nuisance types on the wafer in the selected mode(s). In general, it is expected that a hot scan will find more events than are useful for optimization and that some sort of smart sampling (such as that described further herein) will be required to reduce the data set for actual optimization.

In another such embodiment, selecting the one or more optics modes includes performing a hot scan on the wafer using the inspection system, classifying defects detected using the hot scan, and selecting the one or more optics modes based on the classified defects detected using the hot scan, and the classified defects detected using the hot scan include DOI and nuisance defects. In this manner, the embodiments described herein may include multiple hot scans—one hot scan for optics selection and another (described above) for parameter tuning. The hot scan performed for parameter selection may be performed using the optical mode(s) that were selected for the wafer inspection. Selecting the optical mode(s) in this embodiment may include optics selection with overall scoring, which automatically calculates a single number that specifies how "good" a mode or combination of optics modes is at finding DOI while suppressing nuisance for a given set of defects. This tool eliminates the tedious work of manually comparing the signal-to-noise ratio defect by defect across many modes and significantly reduces the optics selection time. Optics selection with overall scoring may be further performed as described in U.S. Patent Application Publication No. 2011/0320149 to Lee et al., which is incorporated by reference as if fully set forth herein. The embodiments described herein may include any step(s) of any method(s) described in this patent application. Detecting the defects and classifying the defects in this embodiment may be performed as described further herein.

The embodiments described herein depend on the defect samples used for optimization. In particular, the optimization function described further herein uses as input a sample of classified defects. The more representative the sample is of the true population of defects on the wafer, the more likely that the results of the optimization will be valid when applied to additional wafers. Therefore, getting a good classified sample may be critical to this approach working in the field.

In one embodiment, acquiring the information includes sampling the set of classified defects from all defects detected on the wafer such that the set of classified defects includes defects across substantially the entire parameter space of the defect detection method and includes defects having the most diversity from multiple locations on the wafer. Sampling the set of classified defects in this manner may be generally referred to as "smart diversity sampling." The set of defects from which the classified defects are sampled may have been generated by event sampling that includes getting a list of events from the wafer that are meaningful as input to the classification sampling stage. Sampling the set of classified defects from the event sampling results may be performed using classification sampling that involves choosing a subset of items in the event sample that are representative of all of the defect populations on the wafer. Smart diversity sampling combines the advantages of existing smart sampling and diversity sampling, each of which was developed for different purposes. Smart sampling tries to select defect samples across the entire inspection parameter space (i.e., across the entire range of inspection parameter values). Diversity sampling tries to obtain defect samples across other parameter space, which focuses on diversity of defect types. Smart diversity sampling will focus on both inspection parameters and defect types thereby providing better samples for simultaneous sensitivity tuning. The combination of smart and diversity sampling selects a subset of the hot scan data that reflects the true wafer defect population in a way that is meaningful for optimization purposes. The sampling step is important in algorithmic optimization approaches as it determines what types of defects will be found in the final recipe (if a defect type is not represented in the input data then it will not be considered in the optimization). Diversity sampling may be further performed as described in commonly assigned U.S. Pat. No. 7,570,797 to Wang et al. and commonly assigned U.S. patent application Ser. No. 11/146,342 by Dishner et al. filed Jun. 6, 2005, published as U.S. Patent Application Publication No. 2006/0287751 on Dec. 21, 2006, which are incorporated by reference as if fully set forth herein.

The method also includes acquiring an objective for a defect detection method. The defect detection method is to be applied to output generated for wafers by one or more detectors of an inspection system to thereby detect defects on the wafers. The output to which the defect detection method is to be applied may include any output of the inspection system (e.g., output such as data, signals, image data, etc. generated by one or more detectors or one or more detection channels of the inspection system).

A set of objective types may be predefined for a software system. The objective is specified by a user. In one embodiment, the objective is defined as a function of inspection results for DOI and inspection results for nuisance defects. For example, the user may specify a type and an objective for optimization by fixing a nuisance defect rate or count and maximizing the DOI count. In this case, the user also specifies the nuisance defect count or percentage. The user may alternatively select as the optimization objective maximizing (DOI count−nuisance count). Alternatively, the user may select to fix the DOI count or rate and minimize nuisance as the optimization objective. In this case, the user also specifies the DOI count or percentage. The user may specify the optimization objective using the GUI described above. The different objective types capture the logic a user would use to decide if a recipe was "good" or not. For example, the objective specifies how good the defect detection method is in terms of DOI capture and nuisance defect suppression. Additional objective types or modifications to the objectives described above may be identified and characterized based on "non-intuitive" results collected by performing the methods described herein.

In some embodiments, the output to which the defect detection method is to be applied is generated for the wafers by the one or more detectors of the inspection system in a single pass. In another embodiment, the output to which the defect detection method is to be applied is generated for the wafers by the one or more detectors of the inspection system in multiple passes. For example, the embodiments described herein can be applied to single or multi-pass inspection sensitivity optimization. Multi-pass inspection is generally inspection of a single wafer using a set of different sensitivity and optical settings. The goal of multi-pass is to find all DOI while suppressing nuisance. This may be achieved by using the different optical parameters of the various defects to allow each pass to find a different set of defects and then merging the results of the multiple passes back into a single result. Part of this merging may include "post processing" in which data from the different passes is used to further enhance DOI capture or suppress nuisance.

When the embodiments described herein are being used for a multi-pass wafer inspection setup, multiple passes of data may be considered simultaneously against the optimization objective in order to find the combination of passes that best meets the objective. In contrast, current optimization approaches tend to optimize a single pass and then use additional passes to add or subtract from the results of that pass. The simultaneous approach allows for weaknesses in one pass to be offset by strengths of another in a much more comprehensive way than single pass optimization allows. In addition, the embodiments described herein provide significant advantages for multi-pass inspection because, despite all the advantages of multi-pass inspection, the daunting task of individually and manually optimizing n-passes tend to outweigh the advantages for the user. In other words, optimizing a single pass manually is time consuming. Performing the same optimization task n-times requires more work than most users are willing to do. In addition, performing a series of optimizations may not produce a truly optimized result as the interaction between passes may not be easily accounted for manually.

In one embodiment, the output to which the defect detection method is to be applied is generated for the wafers by more than one optics mode of the inspection system. Using multiple optics modes for wafer inspection is becoming more and more common as DOI get smaller and harder to detect. In another embodiment, the output to which the defect detection method is to be applied is generated for the wafers by more than one channel of the inspection system. For an example of multi-channel inspection with the FAST inspection algorithm, the three FAST threshold parameters and three max intensity parameters for all channels may be tuned automatically and simultaneously during the whole optimization process. Multi-channel inspection is a special case of multi-pass inspection. For example, whereas multi-channel uses data separated in space, multi-pass uses data separated in time.

The method also includes selecting one or more parameters of the defect detection method using an optimization function and the information for the set of classified defects such that the one or more parameters satisfy the objective. In this manner, the method may use some of the same input data used in manual recipe optimization approaches. The parameters of the defect detection method that are selected by the method may include any parameters of the defect detection method and may include multi-dimensional parameters. In addition, the defect detection method may be performed using multiple defect detection algorithms, and the method may include performing the method to select one or more parameters for the multiple defect detection algorithms. The manual approach is to tune one parameter at a time. It is a difficult task if some parameters are dependent on each other. The defect detection method parameter(s) are optimized by a global optimization algorithm that explores a multi-dimensional space of all sensitivity parameters and iteratively finds a better parameter set for the user-specified objective until a stopping condition is satisfied. In this manner, the embodiments described herein formulate the simultaneous sensitivity tuning optimization as a global optimization of detection parameter(s) across detection methods (algorithms), detection channels, and detection scans (passes) and solve the optimization with software implementation.

Acquiring the information, acquiring the objective, and selecting the one or more parameters are performed using a computer system. The computer system may be configured as described further herein.

Parameters for the optimization may define an objective "function." The objective "function" may involve multiple parameters, cannot be expressed as an analytic function, and has numerous local minima. For example, the objective "function" may be defined by the defect detection method(s) or algorithm(s) for which parameter(s) are being selected, the parameter(s) that are being selected, classified defects, optimization constraints described further herein, and the objective selected by the user. The defect detection method(s) or algorithm(s) may be the method(s) or algorithm(s) used to detect the set of classified defects. Certain data structures may be used in formulating objective "functions." In one embodiment, the method includes evaluation of the objective "function." The classified defects may be pre-processed and a tree structure or lookup table may be created for fast function evaluation. A parallel mechanism may be used to evaluate multiple defects and/or multiple algorithms at the same time.

In one embodiment, the one or more parameters that are selected include fewer than all parameters of the defect detection method. For example, although the embodiments described herein can optimize all sensitivity parameters automatically, optimization on a subset of sensitivity parameters is allowed. In one such example, the user can select only three FAST threshold parameters to optimize.

Multiple parameters that are optimized may be associated with various constraints. For example, optimization constraints can be the range of detection parameters. The range is determined by their physical meanings. The parameter range can also be derived from all defects used for parameter optimization and detection parameters used to detect these defects. In another embodiment, the optimization function is constrained by requiring threshold values of the defect detection method for two or more channels of the inspection system to be the same. In one such example, two side-channel threshold values can be forced to be the same (e.g., for the FAST and HLAT algorithms) by setting a parameter constraint. In addition, the user can use the GUI described above to select constraints such as suppress unclassified defects and/or optimize multiple detection algorithms. In some embodiments, the optimization function is constrained by one or more ranges of values selected by the user for at least one of the one or more parameters. For example, the user can set the ranges for optimized parameters. In this manner, various parameter constraints can be specified by a user. In one such example, the user may set upper and lower bounds for optimized parameters and to fix segment break values (for MDAT only). The user can also repeat various steps described herein to optimize the sensitivity recipe with different options.

In another embodiment, selecting the one or more parameters include selecting two or more of the one or more parameters simultaneously. For example, the method may be used to optimize multi-dimensional parameters of sensitivity recipes for wafer defect inspection automatically and simultaneously. In this manner, the embodiments described herein may be generally referred to as simultaneous sensitivity tuning (SST) methods and systems.

In one embodiment, the optimization function is a cost function. For example, a well established cost function optimization algorithm such as simulated annealing may be used to solve the optimization problem. The algorithm functions by iterating through a number of randomly chosen solutions in a controlled way that converges on the lowest cost relatively quickly and robustly. The cost function may be any other cost function known in the art.

In another embodiment, the optimization function includes different weights for different defect types included in the set of classified defects. For example, as described further above, a user may specify a weight for each type of defect.

In another embodiment, the method includes performing the method to select one or more parameters for a different defect detection method. For example, the embodiments described herein are general and flexible enough to be used for different recipe tuning problems. In this manner, the embodiments described herein can be performed to select one or more parameters for any defect detection method such as the MDAT, FAST, and HLAT inspection algorithms and can be extended to other algorithms such as inline defect organizer (iDO) ruled-based NEF classifier and multi-pass inspection. In other words, the embodiments described herein are not limited to a specific inspection algorithm. The methodology works for any inspection algorithm as long as a user objective can be expressed in sensitivity parameters. In addition, the embodiments described herein can be extended to other wafer inspection-related setup tasks such as defect binning. Furthermore, the embodiments described herein can be applied to any problem that needs parameter optimization as long as the optimization objectives can be clearly defined.

In some embodiments, the inspection system used to generate the output to which the defect detection method is to be applied is a light-based inspection system having dark field capability, bright field capability, or some combination thereof. For example, the embodiments described herein are general and flexible enough to be used for dark field (DF) inspection systems, bright field (BF) inspection systems, and any other light-based inspection systems known in the art. The inspection system may be further configured as described herein.

SST is a major component for a new recipe setting paradigm called "deterministic" recipe optimization. The concept of deterministic recipe optimization allows the user to do optics selection, hot scan, defect sample selection and recipe optimization using algorithm-powered approaches such as optics selection overall scoring, AutoOSTS, smart diversity sampling and simultaneously sensitivity tuning. In this manner, the one or more parameters for the inspection of the wafer may be selected in a deterministic manner. For example, the embodiments described herein are deterministic in the sense that they use cumulative learning about DOI and nuisance defects on a wafer. In addition, the embodiments described herein introduce the deterministic (versus probabilistic) application of learning from a set of classified defects. As such, the embodiments described herein may be used for "deterministic" inspection recipe setup.

The embodiments described herein have a number of advantages over other methods currently used to select defect detection method parameters. For example, the embodiments described herein can improve the inspection sensitivity performance (e.g., detecting more DOI and suppressing more nuisance defects). The embodiments described herein also reduce human intervention and improve the consistency of the sensitivity performance. However, the deterministic recipe optimization is not intended to replace an expert or to yield the "best" or "definitive" answer in all cases. The results are intended to provide a starting point for experts to continue optimization (e.g., perform additional tuning) or to replace the need for an average user to perform manual optimization in the majority of production, research and development, and engineering application setup cases.

The embodiments described herein will also reduce inconsistency in recipe quality due to subjective factors such as different levels of users' experience, knowledge and skills. Therefore, recipe quality is improved in general. In addition, the embodiments described herein reduce the time for setting sensitivity recipes and therefore overall recipe setup time. For example, hours to days of optimization time for manual tuning can be reduced to seconds to minutes (excluding classification time).

The embodiments described herein also reduce user training and experience required to achieve this improved level of performance. For example, the embodiments described herein take a manual process that requires a relatively high degree of training, experience, and time and converts it to a largely automated process that requires virtually no special training and relatively little time. Algorithm specific training requirements for general users are much reduced. For example, the embodiments described herein redefine the optimization from the user perspective to be one of defect classification rather than parameter tweaking. In one such example, the embodiments described herein provide a set of features that, used together, would allow a user to optimize an inspection recipe, from optics selection to sensitivity parameter selection, using algorithms that rely only on the user's ability to classify defects and specify an optimization objective rather than his/her ability to interpret complicated signal or noise data and manipulate that data to achieve a goal. In this manner, the embodiments described herein change the focus of wafer inspection setup from manual optimization of parameters based on expert data analysis to using algorithmic methods to optimize parameters based on classification of defect data. A user can develop a quality recipe by simply classifying defects rather than manipulating multiple algorithm parameters. As a result, the user does not need to learn the esoteric details of an inspection algorithm and can instead concentrate on the details that matter to them—what defect types are being detected (or suppressed) on the wafer.

The embodiments described herein also provide an approach for fully optimized multi-channel and multi-pass inspections that produce good results in a substantially short amount of time. Tuning multi-channel inspection is no longer limited by manual approaches (best known methods (BKMs)) which work in a subspace of the full, complex, multi-channel optimization space. The embodiments described herein perform full optimization without limitations in manual approaches. In addition, tuning multi-pass inspection is no longer limited by human brain power. Instead, full optimization for all DOI types is limited only by computer power. Furthermore, since the embodiments described herein can select one or more parameters for more than one channel simultaneously, rather than channel by channel as is currently performed, the embodiments described herein will improve recipe sensitivity and optimization efficiency for multi-channel inspection.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method selects one or more parameters for the defect detection method, the method may include storing the selected parameter(s) in an inspection recipe in a storage medium.

Figure 1:
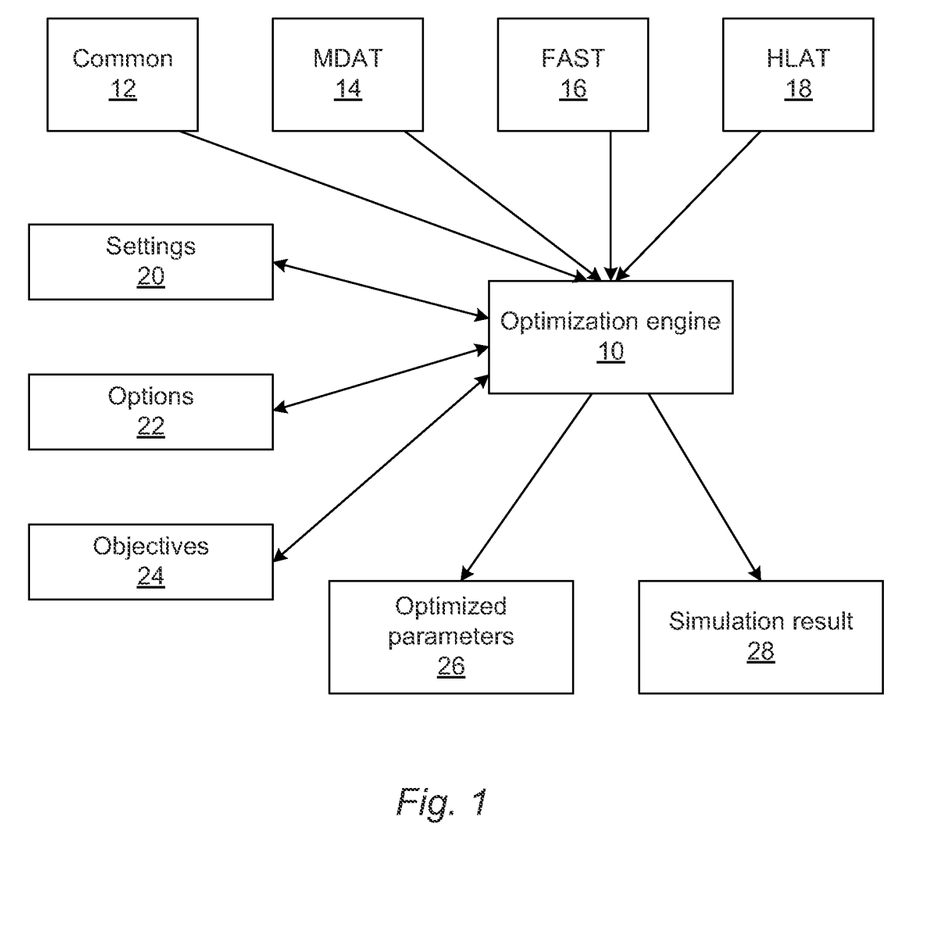
FIG. 1 is a block diagram illustrating one embodiment of an optimization engine, which may be used to perform a computer-implemented method described herein, with various inputs, settings and options, and outputs.

The embodiments described herein may be performed using an optimization engine such as optimization engine 10 shown in FIG. 1. Various parameters of the defect detection method to be optimized may be input to the optimization engine. For example, common parameters 12 such as defect ID, class codes, region ID, and detection parameters used to detect classified defects may be input to the optimization engine. In addition, MDAT parameters 14 such as gray level, offset, and magnitude may be input to the optimization engine. FAST parameters 16 such as Channel1_FAST Threshold, Channel2_FAST Threshold, Channel3_FAST Threshold, Channel1_intensity, Channel2_intensity, and Channel3_intensity may also be input to the optimization engine. Furthermore, HLAT parameters 18 such as Channel1_HLAT Absmin, Channel1_Gradient, Channel1_noise, Channel1_color, Channel2_HLAT Absmin, Channel2_Gradient, Channel2_noise, Channel2_color, Channel3_HLAT Absmin, Channel3_Gradient, Channel3_noise, Channel3_color, Channel1_intensity, Channel2_intensity, and Channel3_intensity may be input to the optimization engine. The common parameters may be input to the optimization engine regardless of the defect detection method for which parameter(s) are being selected while the other parameters that are input may vary depending on the defect detection method for which the parameter(s) are being selected. The parameters described above may be input automatically by software.

The user may also provide various inputs to the optimization engine such as settings 20, which may include, for example, super-class code and weight. The user may also provide options 22 to the optimization engine, which may include, for example, parameter upper and lower bounds, number of segments, suppress unknown defect types, optimize maximum threshold, fix segment break, and force the same values in channels 1 and 2. The user may further select an objective function type and provide objectives 24 to the optimization engine, which may include maximize (DOI count−nuisance count), fix nuisance rate and maximize DOI count, or fix DOI count and minimize nuisance count.

The output of the optimization engine may include optimized parameters 26, which may include any of the optimized parameter(s) described herein, and simulation result 28, which may include detected DOI and nuisance counts, nuisance rate, and reason for not being able to optimize due to insufficient inputs. The optimization engine may be configured to optimize the parameter(s) as described further herein. The optimization engine may be stored on and/or used by a computer system of a wafer inspection system, a computer system of a wafer defect review system, or a stand-alone computer system that is not part of an inspection or review system.

Figure 1A:
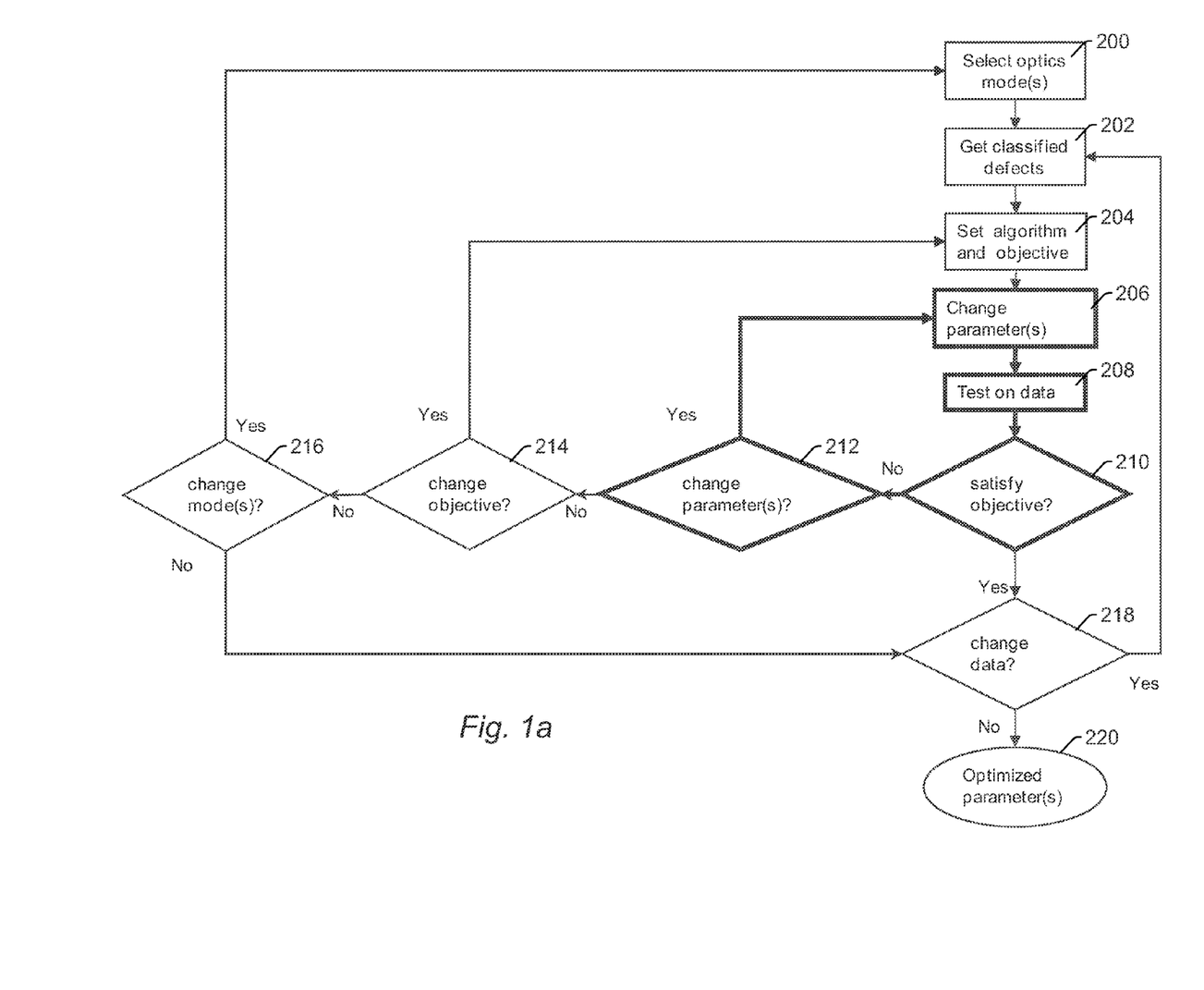
FIG. 1a is a flow chart illustrating one embodiment of a method for sensitivity recipe optimization.

FIG. 1a illustrates one embodiment of a sensitivity recipe optimization. In particular, FIG. 1a illustrates an inner loop and its interaction with other steps in inspection recipe setup. This is an optimization process for single-pass wafer inspection. First, in step 200, the user selects an optics mode or modes. The method may then include getting classified defects in step 202, which may include inspecting the wafer and classifying defects, which serve as the 'ground truth' for parameter optimization. The method also includes setting the defect detection method(s) or algorithm(s) for which parameter(s) are to be selected and the objective, as shown in step 204. Then, the computer system automatically specifies sensitivity parameter(s) as shown in step 206, applies these parameter(s) in inspection simulation as shown in step 208 and checks whether the objective is satisfied as shown in step 210.

If the objective is not satisfied, another round of parameter tuning is performed. The additional round of parameter tuning includes determining if the parameter(s) should be changed as shown in step 212. If the parameter(s) are to be changed, then steps 206, 208, and 210 may be performed again with different parameter(s). Steps 206, 208, 210, and 212 define the inner loop of the method. If the parameter(s) are not to be changed, then the method may include determining if the objective should be changed, as shown in step 214. If the objective is to be changed, then the method may include re-performing steps 204, 206, 208, and 210 with a different objective. If the parameters are not to be changed and the objective is not to be changed, the method includes determining if the optics mode(s) should be changed, as shown in step 216. If the optics mode(s) are to be changed, then the method may include re-performing steps 200, 202, 204, 206, 208, and 210 with different optics mode(s). If the parameter(s) are not to be changed, the objective is not to be changed, and the optics mode(s) are not to be changed, the method includes determining if the data should be changed, as shown in step 218. If it is determined that the parameter(s) are not to be changed, the objective is not to be changed, the optics mode(s) are not to be changed, and the data is not to be changed, then the parameter(s) selected in step 206 are set as optimized parameters 220. If it is determined that the data is to be changed, then steps 202, 204, 206, 208, and 210 are performed with different data.

If the objective is satisfied in step 210, the method includes determining if the data should be changed in step 218. If it is determined that the data is to be changed, then steps 202, 204, 206, 208, and 210 are performed with different data. If it is determined that the data is not to be changed, then the parameter(s) selected in step 206 are set as optimized parameters 220.

In this manner, this parameter tuning process is performed iteratively until the result satisfies the user's objective, which is measured by DOI capture and nuisance suppression. If the result cannot satisfy the detection objective, the user may change the objective, objective "function," detection algorithm, and optics mode. Another round of sensitivity tuning will be performed until the objective is satisfied. The number of iterations in the parameter optimization loop (inner loop) is orders of magnitude larger than the combinations of the two outer loops. The method shown in FIG. 1a may be performed by any of the systems described herein and may include any other step(s) of any other method(s) described herein.

Figure 2:
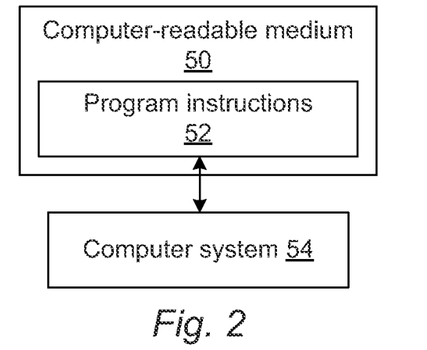
FIG. 2 is a block diagram illustrating one embodiment of a computer-readable medium that includes program instructions executable on a computer system for performing one or more of the computer-implemented methods described herein.

An additional embodiment relates to a non-transitory computer-readable medium storing program instructions executable on a computer system for performing a computer-implemented method for selecting one or more parameters for a defect detection method. One such embodiment is shown in FIG. 2. In particular, as shown in FIG. 2, computer-readable medium 50 includes program instructions 52 executable on computer system 54. The computer-implemented method includes the steps of the method described above. The computer-implemented method for which the program instructions are executable may include any other step(s) described herein.

Program instructions 52 implementing methods such as those described herein may be stored on computer-readable medium 50. The computer-readable medium may be a storage medium such as a read-only memory, a random access memory, a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 3:
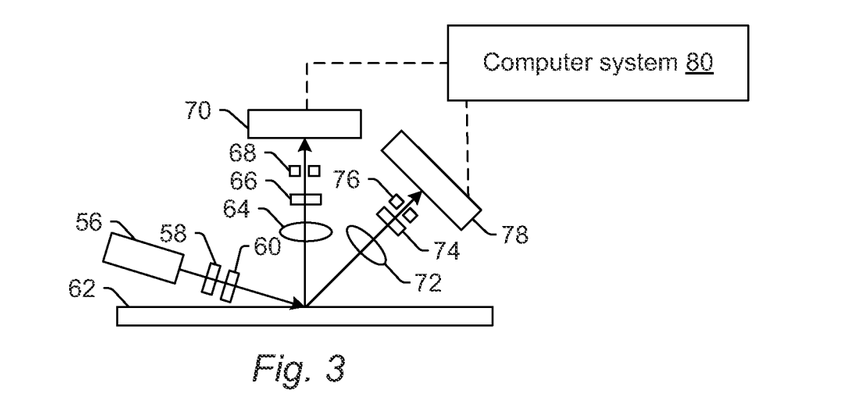
FIG. 3 is a schematic diagram illustrating a side view of one embodiment of a system configured to select one or more parameters for a defect detection method.

Another embodiment relates to a system configured to select one or more parameters for a defect detection method. One embodiment of such a system is shown in FIG. 3. The system includes an inspection system configured to detect defects on a wafer. For example, as shown in FIG. 3, the inspection system includes light source 56. Light source 56 may include any suitable light source known in the art such as a laser.

The inspection system may include filter 58. As shown in FIG. 3, light source 56 may be configured to direct light to filter 58, which may be a spectral filter or any other suitable filter that can be used to alter or select the wavelength(s) of the light from light source 56. In addition, the inspection system may include more than one filter (not shown), each of which may be positioned independently in the path of the light from the light source. Each of the filters may be configured to alter the wavelength(s) of the light from the light source in a different manner. The inspection system may be configured to move the filters into and out of the path of the light from the light source in any suitable manner depending on which wavelength(s) of light is or are selected for illumination of the wafer.

Light from filter 58 may be directed to polarizing component 60, which may include any suitable polarizing component known in the art. In addition, the inspection system may include more than one polarizing component (not shown), each of which may be positioned independently in the path of the light from the filter. Each of the polarizing components may be configured to alter the polarization of the light from the filter in a different manner. The inspection system may be configured to move the polarizing components into and out of the path of the light from the filter in any suitable manner depending on which polarization setting is selected for illumination of the wafer. The polarization setting used for the illumination of the wafer may include any appropriate polarization setting (e.g., p-polarized (P), s-polarized (S), and circularly polarized (C)). In addition, although the light from light source 56 is shown in FIG. 3 to pass through filter 58 and then polarizing component 60, the light from the light source may pass through polarizing component 60 before passing through filter 58. In other words, the positions of the filter and the polarizing component in the path of the light from the light source shown in FIG. 3 may be reversed.

Light exiting polarizing component 60 is directed to wafer 62 at an oblique angle of incidence, which may include any suitable oblique angle of incidence. The inspection system may also include one or more optical components (not shown) that are configured to direct light from light source 56 to filter 58, from filter 58 to polarizing component 60, or from polarizing component 60 to wafer 62. The optical components may include any suitable optical components known in the art such as, but not limited to, a reflective optical component. In addition, the light source, the filter, the polarizing component, and optionally the one or more optical components may be configured to direct the light to the wafer at one or more angles of incidence (e.g., an oblique angle of incidence and/or a substantially normal angle of incidence). The inspection system may be configured to scan the light over the wafer in any suitable manner.

Light scattered from wafer 62 may be collected and detected by multiple channels of the inspection system. For example, light scattered from wafer 62 at angles relatively close to normal may be collected by lens 64. Lens 64 may include a refractive optical element as shown in FIG. 3. In addition, lens 64 may include one or more refractive optical elements and/or one or more reflective optical elements. Light collected by lens 64 may be directed to polarizing component 66, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner. The inspection system may be configured to move the polarizing components into and out of the path of the light collected by the lens in any suitable manner depending on which polarization setting is selected for detection of the light collected by lens 64. The polarization setting used for the detection of the light collected by lens 64 may include any suitable polarization setting (e.g., P, S, and non-polarized (N)).

Light exiting polarizing component 66 may be directed to aperture 68, which may include any suitable aperture known in the art. In addition, the inspection system may include more than one aperture (not shown), each of which may be positioned independently in the path of the light collected by the lens or exiting polarizing component 66. Each of the apertures may be configured to block a portion of the light exiting the polarizing component or the light collected by the lens in a different manner. The inspection system may be configured to move the apertures into and out of the path of the light exiting the polarizing component or the light collected by the lens in any suitable manner depending on which aperture is selected. In addition, although the light collected by lens 64 is shown to pass through polarizing component 66 and then aperture 68, the light collected by the lens may pass through aperture 68 before passing through polarizing component 66. In other words, the positions of the polarizing component and the aperture in the path of the light collected by lens 64 shown in FIG. 3 may be reversed.

Light exiting aperture 68 is directed to detector 70. Detector 70 may include any suitable detector known in the art such as a charge coupled device (CCD) or another type of imaging detector. Detector 70 is configured to generate output that is responsive to the scattered light collected by lens 64 and transmitted by polarizing component 66 and aperture 68 if positioned in the path of the collected scattered light. Therefore, lens 64, polarizing component 66 if positioned in the path of the light collected by lens 64, aperture 68 if positioned in the path of the light exiting polarizing component 66, and detector 70 form one channel of the inspection system. This channel of the inspection system may include any other suitable optical components (not shown) known in the art such as a spectral filter.

Light scattered from wafer 62 at different angles may be collected by lens 72. Lens 72 may be configured as described above. Light collected by lens 72 may be directed to polarizing component 74, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner. The inspection system may be configured to move the polarizing components into and out of the path of the light collected by the lens in any suitable manner depending on which polarization setting is selected for detection of the light collected by lens 72. The polarization setting used for detection of the light collected by lens 72 may include any suitable polarization setting (e.g., P, S, and N).

Light exiting polarizing component 74 may be directed to aperture 76, which may include any suitable aperture known in the art. In addition, the inspection system may include more than one aperture (not shown), each of which may be positioned independently in the path of the light collected by lens 72 or exiting polarizing component 74. Each of the apertures may be configured to block a portion of the light exiting the polarizing component or the light collected by the lens in a different manner. The inspection system may be configured to move the apertures into and out of the path of the light exiting the polarizing component or the light collected by the lens in any suitable manner depending on which aperture is selected. In addition, although the light collected by lens 72 is shown in FIG. 3 to pass through polarizing component 74 and then aperture 76, the light collected by the lens may pass through aperture 76 before passing through polarizing component 74. In other words, the positions of the polarizing component and the aperture in the path of the light collected by lens 72 shown in FIG. 3 may be reversed.

Light exiting aperture 76 is directed to detector 78, which may be configured as described above. Detector 78 is also configured to generate output that is responsive to the collected scattered light that passes through aperture 76 if positioned in the path of the scattered light. Therefore, lens 72, polarizing component 74 if positioned in the path of the light collected by lens 72, aperture 76 if positioned in the path of the light exiting polarizing component 74, and detector 78 may form another channel of the inspection system. This channel may also include any other optical components (not shown) described above. In some embodiments, lens 72 may be configured to collect light scattered from the wafer at polar angles from about 20 degrees to about 70 degrees. In addition, lens 72 may be configured as a reflective optical component (not shown) that is configured to collect light scattered from the wafer at azimuthal angles of about 360 degrees.

The inspection system shown in FIG. 3 may also include one or more other channels (not shown). For example, the inspection system may include an additional channel, which may include any of the optical components described herein such as a lens, one or more polarizing components, one or more apertures, and a detector, configured as a side channel. The lens, the one or more polarizing components, the one or more apertures, and the detector may be further configured as described herein. In one such example, the side channel may be configured to collect and detect light that is scattered out of the plane of incidence (e.g., the side channel may include a lens that is centered in a plane that is substantially perpendicular to the plane of incidence and a detector configured to detect light collected by the lens).

In another example, the inspection system may include an additional channel (not shown), which may include any of the optical components described herein such as a lens, one or more polarizing components, one or more apertures, and a detector, configured as a BF channel. The lens, the one or more polarizing components, the one or more apertures, and the detector may be further configured as described herein. In one such example, the BF channel may be configured to collect and detect light that is specularly reflected from the wafer. In another example, the system may also or alternatively be configured to illuminate the wafer at a substantially normal angle of incidence and to detect light scattered from the wafer using one or more detection channels. In this manner, the system may be configured as a normal incidence DF inspection system.

The system also includes computer system 80. Output generated by the detectors may be provided to computer system 80. For example, the computer system may be coupled to each of the detectors (e.g., by one or more transmission media shown by the dashed lines in FIG. 3, which may include any suitable transmission media known in the art) such that the computer system may receive the output generated by the detectors. The computer system may be coupled to each of the detectors in any suitable manner.

The computer system is configured to acquire information for a set of classified defects, which may be performed as described further herein. The classified defects were detected on a wafer using the inspection system. The classified defects include DOI and nuisance defects. The computer system is also configured to acquire an objective, such as that described herein, for a defect detection method, which may be performed as described further herein. The defect detection method is to be applied to output generated for wafers by one or more detectors of an inspection system to thereby detect defects on the wafers. The objective is specified by a user. In addition, the computer system is configured to select one or more parameters of the defect detection method using an optimization function and the information for the set of classified defects such that the one or more parameters satisfy the objective, which may be performed as described further herein.

The computer system may be configured to perform any other step(s) of any method embodiment(s) described herein. The computer system may be further configured as described herein. The inspection system may also be further configured as described herein. Furthermore, the system may be further configured as described herein.

It is noted that FIG. 3 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as 28XX, 29XX, and Puma 9XXX series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

In some embodiments, a system configured to perform one or more of the computer-implemented methods described herein may include an inspection system such as that described above. However, a system that is configured to perform one or more of the computer-implemented methods described herein may not include an inspection system. For example, the system may include one or more processors or one or more computer systems configured as a stand alone tool. In one such example, the system may include one or more components that are specifically designed (and optionally dedicated) to performing one or more of the computer-implemented methods described herein.

Further modifications and alternative embodiments of various aspects of the invention will be apparent to those skilled in the art in view of this description. For example, computer-implemented methods, computer-readable media, and systems for selecting one or more parameters for a defect detection method are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for selecting one or more parameters for a defect detection method, comprising:
    acquiring information for a set of classified defects, wherein the classified defects were detected on a wafer using an inspection system, and wherein the classified defects comprise defects of interest and nuisance defects;
    acquiring an objective for a defect detection method, wherein the defect detection method is to be applied to output generated for wafers by one or more detectors of an inspection system to thereby detect defects on the wafers, and wherein the objective is specified by a user; and
    selecting two or more parameters of the defect detection method simultaneously using an optimization function and the information for the set of classified defects such that the two or more parameters satisfy the objective, wherein the optimization function is constrained by one or more ranges of values selected by the user for at least one of the two or more parameters, wherein said selecting comprises simultaneously considering multiple passes of data generated for the wafer against the objective to find a combination of the multiple passes that best meets the objective, simultaneously selecting one or more parameters for multiple defect detection algorithms performed in the defect detection method, and simultaneously selecting one or more parameters for multiple detection channels of the inspection system used in the defect detection method, wherein the one or more detectors are included in the multiple detection channels, and wherein acquiring the information, acquiring the objective, and said selecting are performed using a computer system.

2. The method of claim 1, wherein acquiring the information comprises selecting one or more optics modes for the inspection system to be used for the wafer, detecting defects on the wafer using the one or more optics modes, and classifying the detected defects to thereby create the set of classified defects.

3. The method of claim 2, wherein said detecting comprises performing a hot scan on the wafer using the One or more optics modes and one or more detection algorithms.

4. The method of claim 2, wherein selecting the one or more optics modes comprises performing a hot scan on the wafer using the inspection system, detecting defects on the wafer, classifying the defects detected using the hot scan, and selecting the one or more optics modes based on the classified defects detected using the hot scan, and wherein the classified defects detected using the hot scan comprise defects of interest and nuisance defects.

5. The method of claim 1, wherein acquiring the information comprises sampling the set of classified defects from all defects detected on the wafer such that the set of classified defects includes defects across substantially the entire parameter space of the defect detection method and includes defects having the most diversity from various locations on the wafer.

6. The method of claim 1, wherein the objective is defined as a function of inspection results for defects of interest and inspection results for nuisance defects.

7. The method of claim 1, wherein the objective specifies how good the defect detection method is in terms of defect of interest capture and nuisance defect suppression.

8. The method of claim 1, wherein the output to which the defect detection method is to be applied is generated for the wafers by the one or more detectors of the inspection system in the multiple passes.

9. The method of claim 1, wherein the output to which the defect detection method is to he applied is generated for the wafers by more than one optics mode of the inspection system.

10. The method of claim 1, wherein the output to which the defect detection method is to be applied is generated for the wafers by the multiple detection channels of the inspection system.

11. The method of claim 1, wherein the two or more parameters that are selected include fewer than all parameters of the defect detection method.

12. The method of claim 1, wherein the optimization function comprises different weights for different defect types included in the set of classified defects.

13. The method of claim 1, further comprising performing the method to select one or more parameters for a different defect detection method.

14. The method of claim 1, wherein the inspection system used to generate the output to which the defect detection method is to be applied is a light-based inspection system having dark field capability, bright field capability, or some combination thereof.

15. A non-transitory computer-readable medium, storing program instructions executable on a computer system for performing a computer-implemented method for selecting one or more parameters for a defect detection method, wherein the computer-implemented method comprises:
    acquiring information for a set of classified defects, wherein the classified defects were detected on a wafer using an inspection system, and wherein the classified defects comprise defects of interest and nuisance defects;
    acquiring an objective for a defect detection method, wherein the defect detection method is to be applied to output generated for wafers by one or more detectors of an inspection system to thereby detect defects on the wafers, and wherein the objective is specified by a user; and selecting two or more parameters of the defect detection method simultaneously using an optimization function and the information for the set of classified defects such that the two or more parameters satisfy the objective, wherein the optimization function is constrained by one or more ranges of values selected by the user for at least one of the two or more parameters, wherein said selecting comprises simultaneously considering multiple passes of data generated for the wafer against the objective to find a combination of the multiple passes that best meets the objective, simultaneously selecting one or more parameters for multiple defect detection algorithms performed in the defect detection method, and simultaneously selecting one or more parameters for multiple detection channels of the inspection system used in the defect detection method, and wherein the one or more detectors are included in the multiple detection channels.

16. A system configured to select one or more parameters for a defect detection method, comprising:

an inspection system configured to detect defects on a wafer; and a computer system configured to:

acquire information for a set of classified defects, wherein the classified defects were detected on a wafer using the inspection system, and wherein the classified defects comprise defects of interest and nuisance defects;

acquire an objective for a defect detection method, wherein the defect detection method is to be applied to output generated for wafers by one or more detectors of an inspection system to thereby detect defects on the wafers, and wherein the objective is specified by a user; and select two or more parameters of the defect detection method simultaneously using an optimization function and the information for the set of classified defects such that the two or more parameters satisfy the objective, wherein the optimization function is constrained by one or more ranges of values selected by the user for at least one of the two or more parameters, wherein said selecting comprises simultaneously considering multiple passes of data generated for the wafer against the objective to find a combination of the multiple passes that best meets the objective, simultaneously selecting one or more parameters for multiple defect detection algorithms performed in the defect detection method, and simultaneously selecting one or more parameters for multiple detection channels of the inspection system used in the defect detection method, and wherein the one or more detectors are included in the multiple detection channels.

17. The system of claim 16, wherein the computer system is further configured to acquire the information by selecting one or more optics modes for the inspection stem to be used for the wafer, detecting defects on the wafer using the one or more optics modes, and classifying the detected defects to thereby create the set of classified defects.

18. The system of claim 17, wherein said detecting comprises performing a hot scan on the wafer using the one or more optics modes and one or more detection algorithms.

19. The system of claim 17, wherein selecting the one or more optics modes comprises performing a hot scan on the wafer using the inspection system, detecting defects on the wafer, classifying the defects detected using the hot scan, and selecting the one or more optics modes based on the classified defects detected using the hot scan, and wherein the classified defects detected using the hot scan comprise defects of interest and nuisance defects.

20. The system of claim 16, wherein the computer system is further configured to acquire the information by sampling the set of classified defects from all defects detected on the wafer such that the set of classified defects includes defects across substantially the entire parameter space of the defect detection method and includes defects having the most diversity from various locations on the wafer.

21. The system of claim 16, wherein the objective is defined as a function of inspection results for defects of interest and inspection results for nuisance defects.

22. The system of claim 16, wherein the objective specifies how good the defect detection method is in terms of defect of interest capture and nuisance defect suppression.

23. The system of claim 16, wherein the output to which the defect detection method is to be applied is generated for the wafers by the one or more detectors of the inspection system in the multiple passes.

24. The system of claim 16, wherein the output to which the defect detection method is to be applied is generated for the wafers by more than one optics mode of the inspection system.

25. The system of claim 16, wherein the output to which the defect detection method is to be applied is generated for the wafers by the multiple detection channels of the inspection system.

26. The system of claim 16, wherein the two or more parameters that are selected include fewer than all parameters of the defect detection method.

27. The system of claim 16, wherein the optimization function comprises different weights for different defect types included in the set of classified defects.

28. The system of claim 16, wherein the computer system is further configured to select one or more parameters for a different defect detection method.

29. The system of claim 16, wherein the inspection system used to generate the output to which the defect detection method is to be applied is a light-based inspection system having dark field capability, bright field capability, or some combination thereof.

30. The method of claim 1, wherein the optimization function is further constrained by requiring threshold values of the defect detection method for two or more of the multiple detection channels of the inspection system to be the same.

31. The method of claim 1, wherein at least one of the two or more parameters of the defect detection method is dependent on another of the two or more parameters of the defect detection method.

32. The method of claim 1, wherein more than one of the multiple defect detection algorithms is applied to the output generated by a single one of the multiple detection channels of the inspection system in the defect detection method.

33. The system of claim 16, wherein the optimization function is further constrained by requiring threshold values of the defect detection method for two or more of the multiple detection channels of the inspection system to be the same.

34. The system of claim 16, wherein at least one of the two or more parameters of the defect detection method is dependent on another of the two or more parameters of the defect detection method.

35. The system of claim 16, wherein more than one of the multiple defect detection algorithms is applied to the output generated by a single one of the multiple detection channels of the inspection system in the defect detection method.

* * * * *